(12) United States Patent
Chen (10) Patent No.: US 10,456,117 B2
(45) Date of Patent: Oct. 29, 2019

(54) METHOD AND DEVICE FOR ADJUSTING ULTRASONIC CAVITATION INTENSITY

(71) Applicant: VINNO TECHNOLOGY (SUZHOU) CO., LTD., Jiangsu (CN)

(72) Inventor: Huiren Chen, Jiangsu (CN)

(73) Assignee: VINNO TECHNOLOGY (SUZHOU) CO., LTD., Jiangsu (CN)

( * ) Notice: Subject to any disclaimer, the term of this patent is extended or adjusted under 35 U.S.C. 154(b) by 519 days.

(21) Appl. No.: 15/259,307

(22) Filed: Sep. 8, 2016

(65) Prior Publication Data

US 2017/0164932 A1 Jun. 15, 2017

(30) Foreign Application Priority Data

Dec. 10, 2015 (CN) .......................... 2015 1 0917338

(51) Int. Cl.
*A61B 8/00* (2006.01)
*G05B 15/02* (2006.01)
(Continued)

(52) U.S. Cl.
CPC .................. *A61B 8/58* (2013.01); *A61B 8/54* (2013.01); *A61N 7/00* (2013.01); *G05B 15/02* (2013.01);
(Continued)

(58) Field of Classification Search
None
See application file for complete search history.

(56) References Cited

U.S. PATENT DOCUMENTS 10,004,888 B2 * 6/2018 Chapelon ................. A61N 7/02
2007/0167983 A1 * 7/2007 Vago ................... A61H 23/0245
607/2

(Continued)

*Primary Examiner* — Eric C Wai
(74) *Attorney, Agent, or Firm* — Fitch, Even, Tabin & Flannery LLP (57) ABSTRACT

Embodiments of the present disclosure disclose a method and a device for adjusting ultrasonic cavitation intensity. The adjusting method includes: controlling to adjust a $j^{th}$ cavitation coefficient according to an $i^{th}$ cavitation intensity value and a target cavitation intensity value, so as to calculate to obtain an $(i+1)^{th}$ cavitation intensity value; and continuing to control to adjust a $(j+1)^{th}$ cavitation coefficient according to the $(i+1)^{th}$ cavitation intensity value and the target cavitation intensity value, so as to calculate to obtain an $(i+2)^{th}$ cavitation intensity value if the absolute value of a difference between the $(i+1)^{th}$ cavitation intensity value and the target cavitation intensity value is greater than a set threshold value, and ending the method when it is determined that the absolute value of the difference between the $(i+1)^{th}$ cavitation intensity value and the target cavitation intensity value is less than or equal to the set threshold value.

12 Claims, 3 Drawing Sheets

(51) Int. Cl.
*A61N 7/00* (2006.01)
*A61B 90/00* (2016.01)
*A61B 17/22* (2006.01)
*A61B 17/00* (2006.01)

(52) U.S. Cl.
CPC .............. *A61B 2017/00172* (2013.01); *A61B 2017/22008* (2013.01); *A61B 2090/378* (2016.02); *A61N 2007/0039* (2013.01)

(56) References Cited

U.S. PATENT DOCUMENTS

2016/0015953 A1* 1/2016 Silberg .............. A61M 37/0092
  604/22
2016/0339273 A1* 11/2016 Al Mayiah .............. A61N 7/02

* cited by examiner

METHOD AND DEVICE FOR ADJUSTING ULTRASONIC CAVITATION INTENSITY

TECHNICAL FIELD

Embodiments of the present disclosure relate to the field of ultrasonic transmission technologies, and particularly relate to a method and a device for adjusting ultrasonic cavitation intensity.

TECHNICAL BACKGROUND

Ultrasonic equipments are applied to fields of medical ultrasonic imaging and therapy on basis of cavitation effect of ultrasonic waves, and can also be applied as cleaning instruments. Medical ultrasonic equipments are used for medical therapy on basis of a transient cavitation phenomenon; partial high-temperature and high-pressure phenomena will be generated due to transient cavitation, accompanied by generation of a strong shock wave, a high-speed micro-jet and free radicals; and a great destructive effect can be formed on structures of normal cells and biological activities of enzymes, and meanwhile, tumour cells can be effectively killed.

Cavitation bursting intensity of the transient cavitation is an important factor influencing safety and efficiency in clinical use of medical ultrasonic equipments. There are many factors influencing the cavitation bursting intensity, such as transmit frequency, transmit voltage, transmit pulse length, liquid properties and the like. In the related art, ultrasonic equipments achieve a purpose of controlling to adjust the cavitation bursting intensity in a manner of forward mapping, namely, operators passively change the cavitation bursting intensity by adjusting parameters such as the transmit frequency, the transmit voltage, the transmit pulse length, transmit pulse repetition frequency, transmit pulse continuous times and the like.

In actual clinical use, when operators need to change the cavitation bursting intensity to B from A, it is quite difficult to quickly and accurately adjust such a set of combined parameters of the transmit frequency, the transmit voltage, the transmit pulse length, the transmit pulse repetition frequency, the transmit pulse continuous times and the like; and however, operators can only adjust and try parameters one by one, which is time-consuming and effects are hard to ensure, so that patients may miss best imaging and therapy.

SUMMARY

Embodiments of the present disclosure provide a method and a device for adjusting ultrasonic cavitation intensity, so as to solve a problem of time consuming of adjusting process and poor adjusting effect.

In a first aspect, embodiments of the present disclosure provide a method for adjusting ultrasonic cavitation intensity, including:

controlling to adjust a $j^{th}$ cavitation coefficient according to an $i^{th}$ cavitation intensity value and a target cavitation intensity value, so as to calculate to obtain an $(i+1)^{th}$ cavitation intensity value, where $i=0, 1, 2 \ldots, j=1, 2, \ldots, n$, and $7 \geq n \geq 2$; and continuing to control to adjust a $(j+1)^{th}$ cavitation coefficient according to the $(i+1)^{th}$ cavitation intensity value and the target cavitation intensity value, so as to calculate to obtain an $(i+2)^{th}$ cavitation intensity value if the absolute value of a difference between the $(i+1)^{th}$ cavitation intensity value and the target cavitation intensity value is greater than a set threshold value, and ending the method when it is determined that the absolute value of the difference between the $(i+1)^{th}$ cavitation intensity value and the target cavitation intensity value is less than or equal to the set threshold value.

Further, the $j^{th}$ cavitation coefficient includes any one or more of transmit frequency coefficient k1, pulse length coefficient k2, pulse frequency coefficient k3, pulse times coefficient k4, scanning line density coefficient k5, region-of-interest size coefficient k6, and transmit voltage coefficient k7.

Further, a calculation formula of a cavitation intensity value Q is specifically as follows.

$$Q = f \begin{pmatrix} ((1+k1) \times \text{Frequency})^{-1/2} \times (1+k2) \times \text{Pulse Length}, \\ (1+k3) \times PRF \times (1+k4) \times \text{Pulse Times}, \\ (1+k5) \times \text{Line Density} \times ((1+k6) \times ROI \text{ Size})^{-1}, \\ \frac{1}{2} \times P((1+k7) \times \text{Transmit Voltage})^2 / Z \end{pmatrix}$$

where the Frequency represents ultrasonic transmit frequency, the Pulse Length represents ultrasonic transmit pulse length, the PRF represents ultrasonic transmit pulse repetition frequency, the Pulse Times represents ultrasonic transmit pulse continuous times, the Line Density represents ultrasonic transmit scanning line density, the ROI Size represents ultrasonic cavitation busting region-of-interest size, and the Transmit Voltage represents ultrasonic transmit voltage.

Further, controlling to adjust the $j^{th}$ cavitation coefficient according to the $i^{th}$ cavitation intensity value and the target cavitation intensity value, so as to calculate to obtain the $(i+1)^{th}$ cavitation intensity value, includes:

judging whether the target cavitation intensity value is greater than the $i^{th}$ cavitation intensity value;

controlling to correspondingly adjust the value of the $j^{th}$ cavitation coefficient as a $j^{th}$ coefficient value set according to a set rule if the target cavitation intensity value is greater than the $i^{th}$ cavitation intensity value, so as to calculate to obtain the $(i+1)^{th}$ cavitation intensity value; and, controlling to correspondingly adjust the value of the $j^{th}$ cavitation coefficient to a negative $j^{th}$ coefficient value set according to a set rule if the target cavitation intensity value is not greater than the $i^{th}$ cavitation intensity value, so as to calculate to obtain the $(i+1)^{th}$ cavitation intensity value.

Further, the set rule includes: a $j^{th}$ coefficient value in a next adjustment is $1/m$ of $j^{th}$ coefficient value in a previous adjustment, where $m>1$.

Further, an absolute value of the $j^{th}$ coefficient value is greater than or equal to 0, and less than or equal to 1.

Further, after calculating to obtain the $(i+1)^{th}$ cavitation intensity value, the method further includes:

calculating a difference between the $(i+1)^{th}$ cavitation intensity value and the target cavitation intensity value and judging whether an absolute value of the difference is less than or equal to the set threshold value.

Further, the method further includes: controlling to stop the adjustment for the cavitation coefficients if the absolute value of the difference between the $(i+1)^{th}$ cavitation intensity value and the target cavitation intensity value is less than or equal to the set threshold value.

Further, the set threshold value is 0.001.

In a second aspect, embodiments of the present disclosure further provide a device for adjusting ultrasonic cavitation intensity, including:

at least one processor; and a memory communicably connected with the at least one processor for storing instructions executable by the at least one processor, wherein execution of the instructions by the at least one processor causes the at least one processor to:

control to adjust a $j^{th}$ cavitation coefficient according to an $i^{th}$ cavitation intensity value and a target cavitation intensity value, so as to calculate to obtain an $(i+1)^{th}$ cavitation intensity value, where i=0, 1, 2 . . . , j=1, 2, . . . , n, and 7≥n≥2; and continue to control to adjust a $(j+1)^{th}$ cavitation coefficient according to the $(i+1)^{th}$ cavitation intensity value and the target cavitation intensity value, so as to calculate to obtain an $(i+2)^{th}$ cavitation intensity value if an absolute value of a difference between the $(i+1)^{th}$ cavitation intensity value and the target cavitation intensity value is greater than a set threshold value, and end the method when it is determined that the absolute value of the difference between the $(i+1)^{th}$ cavitation intensity value and the target cavitation intensity value is less than or equal to the set threshold value.

In the present disclosure, the $(i+1)^{th}$ cavitation intensity value is obtained through calculation by adjusting the $j^{th}$ cavitation coefficient according to the $i^{th}$ cavitation intensity value and the target cavitation intensity value, and subsequent judgment is carried out; if the absolute value of the difference between the $(i+1)^{th}$ cavitation intensity value and the target cavitation intensity value is greater than the set threshold value, the method returns, the calculation for the cavitation intensity value is continued and the judgement is carried out, until it is determined that the absolute value of the difference between the obtained cavitation intensity value and the target cavitation intensity value is less than or equal to the set threshold value. In the present disclosure, the target cavitation intensity value is known, the purpose of adjusting an initial cavitation intensity value as the target cavitation intensity value by adjusting cavitation coefficients is achieved, and cavitation coefficients are adjusted according to the target cavitation intensity value in a manner of reverse mapping. The adjusting manner has advantages of high adjusting speed and quite small adjusting error, and solves defects in the related art.

DESCRIPTION OF DRAWINGS

In order to illustrate technical solutions in embodiments of the present disclosure more clearly, drawings which are needed in descriptions of embodiments are simply introduced below. Apparently, the drawings in the descriptions below are merely a part of embodiments of the present disclosure, based on which other drawings may also be obtained by those ordinary skilled in the art without any creative effort.

DETAILED DESCRIPTION

In order to make the purposes, technical solutions and advantages of the present disclosure more clear, technical solutions of the present disclosure are clearly and completely described below by reference to the drawings in embodiments of the present disclosure through implementations. Apparently, embodiments described are a part of embodiments of the present disclosure, rather than all embodiments. Based on embodiments in the present disclosure, all other embodiments obtained by those ordinary skilled in the art without any creative effort shall still fall within the scope of protection of the present disclosure.

Embodiment 1

Figure 1:
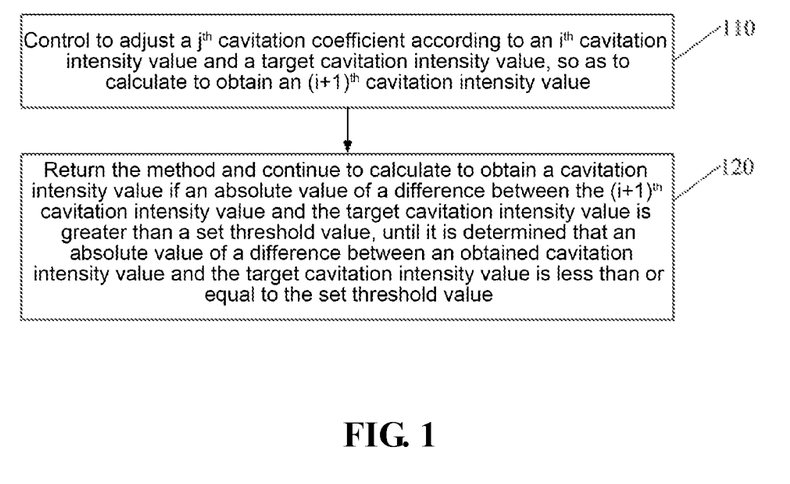
FIG. 1 is a flow diagram illustrating a method for adjusting ultrasonic cavitation intensity provided by embodiment 1 of the present disclosure.

FIG. 1 is a flow diagram illustrating a method for adjusting ultrasonic cavitation intensity provided by embodiment 1 of the present disclosure. Technical solutions of the present embodiment is applicable to a case of automatically adjusting cavitation parameters through a known target cavitation intensity value; and the method can be executed by a device for adjusting ultrasonic cavitation intensity, and the adjusting device is configured in an ultrasonic equipment.

A method for adjusting ultrasonic cavitation intensity provided by the present embodiment specifically includes following steps.

In S110, a $j^{th}$ cavitation coefficient is adjusted by controlling according to an $i^{th}$ cavitation intensity value and a target cavitation intensity value, so as to calculate to obtain an $(i+1)^{th}$ cavitation intensity value, where i=0, 1, 2 . . . , j=1, 2, . . . , n, and 7≥n≥2.

As described above, a current initial cavitation intensity value to be adjusted and a needed cavitation intensity value input by an operator are displayed on a panel of the ultrasonic equipment, then the device for adjusting ultrasonic cavitation intensity (referred to as an adjusting device) acquires the current initial cavitation intensity value to be adjusted and the input needed cavitation intensity value; and then the adjusting device takes the initial cavitation intensity value to be adjusted as a $0^{th}$ cavitation intensity value, and takes the needed cavitation intensity value as a target cavitation intensity value. It can be seen that the adjusting device has a function of automatically adjusting the initially-displayed $0^{th}$ cavitation intensity value as the target cavitation intensity value input by the operator.

Cavitation coefficients are coefficients of cavitation parameters, and cavitation parameters influence the cavitation intensity value; thus change of cavitation coefficients changes cavitation parameter values corresponding to cavitation coefficients, and then the cavitation intensity value is changed, so that the purpose of changing the cavitation intensity value is achieved by adjusting cavitation coefficients. There are a plurality of cavitation parameters influencing the cavitation intensity value, and cavitation coefficients are in one-to-one correspondence with cavitation parameters; and by taking seven cavitation parameters as an example here, number of adjustable cavitation coefficients is not greater than seven. Those skilled in the art can understand that the $(i+1)^{th}$ cavitation intensity value obtained through calculation and/or cavitation parameter values can also be optionally displayed on the panel of the ultrasonic equipment in real time and viewed by the operator, and more than or less than seven cavitation parameters can also be optionally adjusted. The cavitation intensity value here means an ultrasonic cavitation bursting intensity value of the ultrasonic equipment, and cavitation parameters are parameters influencing the ultrasonic cavitation bursting intensity value.

Specifically, the adjusting device controls to adjust a first cavitation coefficient according to the $0^{th}$ cavitation intensity value and the target cavitation intensity value, and calculates to obtain a first cavitation intensity value. The first cavitation intensity value is detected through subsequent steps; and the adjusting device controls, if it is decided that further adjustment is needed, to adjust a second cavitation coefficient according to the first cavitation intensity value and the target cavitation intensity value, and calculates to obtain a second cavitation intensity value; and so on, until the adjusting device controls to stop adjusting.

In the above operation, adjustment for cavitation coefficients is carried out according to the $i^{th}$ cavitation intensity value and a known target cavitation intensity value, so as to achieve the purpose of adjusting the cavitation intensity value, namely, cavitation coefficients are adjusted according to the known target cavitation intensity in a manner of reverse mapping, so that the initial cavitation intensity value is adjusted as the target cavitation intensity value.

In S120, the method returns and the calculation is continued to obtain a cavitation intensity value if an absolute value of a difference between the $(i+1)^{th}$ cavitation intensity value and the target cavitation intensity value is greater than a set threshold value, until it is determined that an absolute value of a difference between an obtained cavitation intensity value and the target cavitation intensity value is less than or equal to the set threshold value.

As described above, after calculating to obtain the $(i+1)^{th}$ cavitation intensity value by adjusting the $j^{th}$ cavitation coefficient, the adjusting device carries out difference calculation on the $(i+1)^{th}$ cavitation intensity value obtained through calculation and the target cavitation intensity value, where the set threshold value is preset in the adjusting device, and then the adjusting device judges whether to continue adjusting according to a comparison result of the difference and the set threshold value. Specifically, after calculating to obtain the difference, the adjusting device judges whether an absolute value of the difference is greater than the set threshold value; if the absolute value of the difference is greater than the set threshold value, it is indicated that the difference between the $(i+1)^{th}$ cavitation intensity value and the target cavitation intensity value is large, and adjustment for cavitation coefficients needs to be continued, and the method returns to step S110 and calculation for subsequent cavitation intensity values is continued.

Initially, i=0, and then a difference calculation is carried out on the first cavitation intensity value obtained through calculation and the target cavitation intensity value for the first time; and if an absolute value of the difference is greater than the set threshold value, the method returns and the second cavitation intensity value is obtained through calculation according to the first cavitation intensity value and the target cavitation intensity value. When an absolute value of a difference between the second cavitation intensity value and the target cavitation intensity value is greater than the set threshold value, the method returns and calculation is continued to obtain a third cavitation intensity value; and so on, until it is determined that an absolute value of a difference between an obtained cavitation intensity value and the target cavitation intensity value is less than or equal to the set threshold value, then the adjusting process is completed and adjustment is stopped by controlling; and at this moment, the cavitation intensity value obtained through adjustment is taken as a finally-determined cavitation intensity value. That is to say, when an absolute value of a difference between the finally-determined cavitation intensity value and the target cavitation intensity value is less than or equal to the set threshold value, it is decided that the adjustment is successful, namely, the initial $0^{th}$ cavitation intensity value is already adjusted as the target cavitation intensity value.

In the above operation, whether the absolute value of the difference between the $(i+1)^{th}$ cavitation intensity value and the target cavitation intensity value is greater than the set threshold value is taken as a basis for judging whether the adjustment is successful; and the steps 110 to 120 are circulated when the adjustment is unsuccessful, until the adjustment is successful, namely, the absolute value of the difference between the finally-determined cavitation intensity value and the target cavitation intensity value is less than or equal to the set threshold value. The adjusting device automatically adjusts the cavitation intensity value through set circulation steps, so that adjusting speed is high and adjusting error is quite small.

In the present embodiment, the $(i+1)^{th}$ cavitation intensity value is obtained through calculation by adjusting the $j^{th}$ cavitation coefficient according to the $i^{th}$ cavitation intensity value and the target cavitation intensity value, and subsequent judgment is carried out; if the absolute value of the difference between the $(i+1)^{th}$ cavitation intensity value and the target cavitation intensity value is greater than the set threshold value, the method returns, the calculation for the cavitation intensity value is continued and the judgement is carried out, until it is determined that the absolute value of the difference between the obtained cavitation intensity value and the target cavitation intensity value is less than or equal to the set threshold value. In the present embodiment, the target cavitation intensity value is known, the purpose of adjusting an initial cavitation intensity value as the target cavitation intensity value by adjusting cavitation coefficients is achieved, and cavitation coefficients are adjusted according to the target cavitation intensity value in a manner of reverse mapping. The adjusting manner has advantages of high adjusting speed and quite small adjusting error.

Embodiment 2

Technical solutions of the present embodiment is applicable to a case of automatically adjusting cavitation parameters through a known target cavitation intensity value; and the method can be executed by a device for adjusting ultrasonic cavitation intensity, and the adjusting device is configured in an ultrasonic equipment.

It should be noted here that there are many parameters influencing the cavitation intensity value. In the present embodiment, only seven cavitation parameters are selected as main factors influencing the cavitation intensity value, and the seven cavitation parameters specifically include: ultrasonic transmit frequency (Frequency), ultrasonic transmit pulse length (Pulse length), ultrasonic transmit pulse repetition frequency (PRF), ultrasonic transmit pulse continuous times (Pulse times), ultrasonic transmit scanning line density (Line density), ultrasonic cavitation busting region-of-interest size (ROI size), and ultrasonic transmit voltage (Transmit voltage). Correspondingly, each cavitation parameter corresponds to a cavitation coefficient, which is respectively as follows: transmit frequency coefficient k1, pulse length coefficient k2, pulse frequency coefficient k3, pulse times coefficient k4, scanning line density coefficient k5, region-of-interest size coefficient k6, and transmit voltage coefficient k7. Those skilled in the art can understand that parameters influencing the cavitation intensity value further include liquid temperature, liquid surface tension and the like, and more than or less than seven cavitation parameters can also be selected as main parameters, which is not described redundantly here. In the present embodiment, only influence of the above seven cavitation parameters on the cavitation intensity value is taken as an example.

For any adjusting process, adjustment to only one of cavitation coefficients is allowable, and simultaneous adjustment to at least two cavitation coefficients is also allowable. Therefore, the $j^{th}$ cavitation coefficient includes at least one cavitation coefficient to be adjusted. It can be seen that the $j^{th}$ cavitation coefficient includes: any one or more of transmit frequency coefficient k1, pulse length coefficient k2, pulse frequency coefficient k3, pulse times coefficient k4, scanning line density coefficient k5, region-of-interest size coefficient k6, and transmit voltage coefficient k7.

Here, if a case is taken as an example that adjusting objects of a first cavitation coefficient include k1, k6 and k7, adjusting objects of a second cavitation coefficient include k2 and k5, an adjusting object of a third cavitation coefficient includes k3, and an adjusting object of a fourth cavitation coefficient includes k4, when a fifth cavitation intensity value is calculated, the fifth cavitation intensity value can be obtained through calculation by controlling to adjust k1, k6 and k7 according to the fourth cavitation intensity value and the target cavitation intensity value. Those skilled in the art can understand that adjusting objects of a $j^{th}$ cavitation coefficient can also be set according to other sequences or amounts, which is not described redundantly here.

In the present embodiment, it is known that factors influencing the cavitation intensity value are set to mainly include seven cavitation parameters which respectively are Frequency, Pulse Length, PRF, Pulse Times, Line Density, ROI Size and Transmit Voltage. Then the cavitation intensity value is set as Q, and a function equation of Q and the seven cavitation parameters is shown in following formula (1):

$$Q = f\begin{pmatrix} \text{Frequency, PulseLength, } PRF, \text{ Pulse Times,} \\ \text{Transmit Voltage, Line Density, } ROI \text{ Size} \end{pmatrix} \quad (1)$$

$$\approx \frac{1}{2} \times (P(\text{Transmit Voltage})^2/Z) \times \text{Pulse Length} \times PRF \times$$

$$\text{Pulse Times} \times \text{Line Density} \times \text{Frequency}^{-1/2} \times ROI \text{ Size}^{-1}$$

where the P(Transmit Voltage)∝Transmit Voltage represents an acoustic pressure, and the Z represents an acoustic impedance (the Z is a constant when substance is determined). It is known that the adjusting device obtains the target cavitation intensity value; therefore, the function equation is converted to the known Q, and a group of optional solutions Frequency, Pulse Length, PRF, Pulse Times, Transmit Voltage, Line Density and ROI Size enabling the value of the function to be Q is solved.

In order to simplify combination of the formula (1), cavitation parameters can be combined here according to influence of cavitation parameters on the cavitation intensity value, and then function equation of Q is converted to following formula (2) from the formula (1):

$$Q = f\begin{pmatrix} g_1(\text{Frequency, Pulse Length}), \\ g_2(PRF, \text{ Pulse Times}), \\ g_3(\text{Line Density, } ROI \text{ Size}), \\ g_4(\text{Transmit Voltage}) \end{pmatrix} \quad (2)$$

where function equations of $g_1$(Frequency, Pulse Length), $g_2$(PRF, Pulse Times), $g_3$(Line Density, ROI Size) and $g_4$(Transmit Voltage) are as follows:

$g_1$(Frequency,Pulse Length)=$((1+k1)\times$Frequency$)^{-1/2}\times(1+k2)\times$Pulse Length, $g_2$(PRF,Pulse Times)=$(1+k3)\times$PRF$\times(1+k4)\times$Pulse Times, $g_3$(Line Density,ROI Size)=$(1+k5)\times$Line Density$\times((1+k6)\times$ROI Size$)^{-1}$, $g_4$(Transmit Voltage)=$(\frac{1}{2})\times P((1+k7)\times$Transmit Voltage$)^2/Z$.

In conclusion, calculation formula of the cavitation intensity value Q is specifically shown in following formula (3):

$$Q = f\begin{pmatrix} ((1+k1) \times \text{Frequency})^{-1/2} \times (1+k2) \times \text{Pulse Length,} \\ (1+k3) \times PRF \times (1+k4) \times \text{Pulse Times,} \\ (1+k5) \times \text{Line Density} \times ((1+k6) \times ROI \text{ Size})^{-1}, \\ \frac{1}{2} \times P((1+k7) \times \text{Transmit Voltage})^2/Z \end{pmatrix} \quad (3)$$

where the Frequency represents ultrasonic transmit frequency, the Pulse Length represents ultrasonic transmit pulse length, the PRF represents ultrasonic transmit pulse repetition frequency, the Pulse Times represents ultrasonic transmit pulse continuous times, the Line Density represents ultrasonic transmit scanning line density, the ROI Size represents ultrasonic cavitation busting region-of-interest size, and the Transmit Voltage represents ultrasonic transmit voltage. The cavitation intensity value obtained through calculation is enabled to be close to or equal to the target cavitation intensity value by adjusting k1 to k7 according to the above formula (3).

Figure 2:
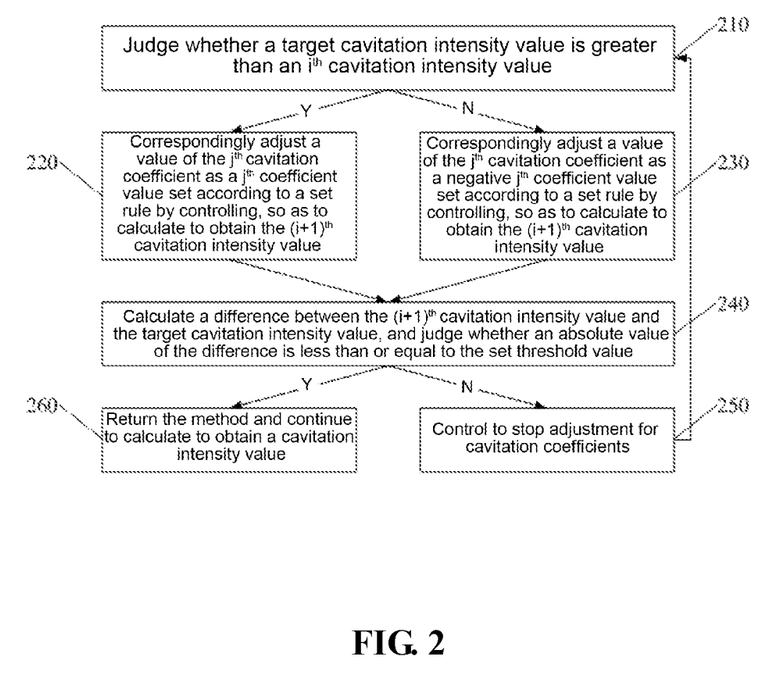
FIG. 2 is a flow diagram illustrating a method for adjusting ultrasonic cavitation intensity provided by embodiment 2 of the present disclosure.

Based on the above, as shown in FIG. 2, a method for adjusting ultrasonic cavitation intensity provided by the present embodiment specifically includes following steps.

In S210, whether a target cavitation intensity value is greater than an $i^{th}$ cavitation intensity value is judged.

As described above, an adjusting device acquires a needed target cavitation intensity value input by operator on a panel of an ultrasonic equipment, and directly acquires an initial cavitation intensity value as the $0^{th}$ cavitation intensity value, and the first cavitation intensity value can be obtained through calculation according to the $0^{th}$ cavitation intensity value and the target cavitation intensity value, and so on; and the $i^{th}$ cavitation intensity value is known. Therefore, the adjusting device can judge whether the target cavitation intensity value is greater than the $i^{th}$ cavitation intensity value according to the known $i^{th}$ cavitation intensity value and target cavitation intensity value, and execute subsequent operations on the basis of a judgement result.

Here, if the target cavitation intensity value is greater than the $i^{th}$ cavitation intensity value, S220 is executed; and if the target cavitation intensity value is less than or equal to the $i^{th}$ cavitation intensity value, the method jumps to execute S230.

In S220, if the target cavitation intensity value is greater than the $i^{th}$ cavitation intensity value, a value of the $j^{th}$ cavitation coefficient is correspondingly adjusted as a $j^{th}$ coefficient value set according to a set rule by controlling, so as to calculate to obtain the $(i+1)^{th}$ cavitation intensity value.

As described above, a case is taken as an example that adjusting objects of the second cavitation coefficient include k3 and k4; and when the target cavitation intensity value is greater than the first cavitation intensity value, a specific process of adjusting a value of the second cavitation coefficient is as follows: a current value of k3 is adjusted as a coefficient value of k3 set according to a set rule, and a current value of k4 is adjusted as a coefficient value of k4 set according to a set rule. The $(i+1)^{th}$ cavitation intensity value is obtained through calculation and then S240 is executed.

If the coefficient value of k3 is a3, and the coefficient value of k4 is −a4; the current value of k3 is adjusted as a3, and the current value of k4 is adjusted as −a4 when the target cavitation intensity value is greater than the first cavitation intensity value. Those skilled in the art can understand that adjustment for the $j^{th}$ cavitation coefficient means that a value of each adjusting object in the $j^{th}$ cavitation coefficient is adjusted as a corresponding coefficient value, and at least one adjusting object is included in the $j^{th}$ cavitation coefficient here.

In S230, if the target cavitation intensity value is not greater than the $i^{th}$ cavitation intensity value, a value of the $j^{th}$ cavitation coefficient is correspondingly adjusted as a negative $j^{th}$ coefficient value set according to a set rule by controlling, so as to calculate to obtain the $(i+1)^{th}$ cavitation intensity value.

As described above, a case is taken as an example that adjusting objects of the second cavitation coefficient include k3 and k4; and when the target cavitation intensity value is less than or equal to the first cavitation intensity value, a specific process of adjusting a value of the second cavitation coefficient is as follows: a current value of k3 is adjusted as a negative coefficient value of k3 set according to a set rule, and a current value of k4 is adjusted as a negative coefficient value of k4 set according to a set rule. The $(i+1)^{th}$ cavitation intensity value is obtained through calculation and then S240 is executed.

If the coefficient value of k3 is a3, and the coefficient value of k4 is −a4; in the above operation, the current value of k3 is adjusted as −a3, and the current value of k4 is adjusted as a4. Those skilled in the art can understand that adjustment for the $j^{th}$ cavitation coefficient means that a value of each adjusting object in the $j^{th}$ cavitation coefficient is adjusted as a corresponding coefficient value, and at least one adjusting object is included in the $i^{th}$ cavitation coefficient here.

In S240, a difference between the $(i+1)^{th}$ cavitation intensity value and the target cavitation intensity value is calculated, and whether an absolute value of the difference is less than or equal to the set threshold value is judged.

As described above, the target cavitation intensity value is known and the $(i+1)^{th}$ cavitation intensity value is obtained through calculation, and then the adjusting device calculates a difference between the $(i+1)^{th}$ cavitation intensity value and the target cavitation intensity value. The set threshold value is also preset in the adjusting device, and the adjusting device judges whether the absolute value of the difference is less than or equal to the set threshold value according to the set threshold value; and if the absolute value of the difference is not less than or equal to the set threshold value, S250 is executed; if the absolute value of the difference is less than or equal to the set threshold value, the method jumps to execute S260.

In S250, the method returns and the calculation is continued to obtain a cavitation intensity value if the absolute value of the difference between the $(i+1)^{th}$ cavitation intensity value and the target cavitation intensity value is greater than the set threshold value, until it is determined that an absolute value of a difference between an obtained cavitation intensity value and the target cavitation intensity value is less than or equal to the set threshold value.

In S260, adjustment for cavitation coefficients is stopped by controlling if the absolute value of the difference between the $(i+1)^{th}$ cavitation intensity value and the target cavitation intensity value is less than or equal to the set threshold value.

As described above, when the absolute value of the difference between the $(i+1)^{th}$ cavitation intensity value and the target cavitation intensity value is less than or equal to the set threshold value, it is considered that the $(i+1)^{th}$ cavitation intensity value is close to the target cavitation intensity value and the difference therebetween is negligible; and at this moment, the adjusting device determines that the currently-obtained $(i+1)^{th}$ cavitation intensity value can be taken as the cavitation intensity value needed by the operator. Therefore, the adjusting device controls to stop the adjustment for cavitation coefficients, namely, the adjusting process is completed.

It should be noted that the set threshold value is optionally 0.001; and those skilled in the art can understand that the set threshold value can be automatically set according to different use conditions of the ultrasonic equipment.

On the basis of the above technical solution, it should be noted that the set rule optionally includes the following. A $j^{th}$ coefficient value in a next adjustment is 1/m of a $i^{th}$ coefficient value in a previous adjustment, where m>1. A case is taken as an example that a cavitation intensity value corresponds to four cavitation coefficients and adjusting objects of a second cavitation coefficient include k3 and k4; the second cavitation coefficient is used for calculating a second cavitation intensity value while being adjusted for a first time; and at this moment, a coefficient value of k3 in the second cavitation coefficient is adjusted as a3, and a coefficient value of k4 is adjusted as −a4; and then the second cavitation coefficient is used for calculating a sixth cavitation intensity value while being adjusted for a second time, a coefficient value of k3 in the second cavitation coefficient is adjusted as $(1/m)*a3$, and a coefficient value of k4 is adjusted as $(1/m)*(-a4)$. Those skilled in the art can understand that the m can be adjusted according to different adjusting sequences; and for example, m=1.5 is set in a second adjustment, m=2 is set in a third adjustment and the like, and the m can be appropriately adjusted according to conditions.

On the basis of the above technical solution, it should be noted that the absolute value of the $j^{th}$ coefficient value is greater than or equal to 0, and less than or equal to 1. The second cavitation coefficient is taken as an example, where $0 \le |a3|$ and $|a4| \le 1$, and the coefficient value can be automatically adjusted in a range from 0 to 1.

In the present embodiment, the adjusting device carries out reverse mapping according to the target cavitation intensity value and adjusts coefficients of cavitation parameters influencing the cavitation intensity value, so that the finally-determined cavitation intensity value is close to the target cavitation intensity value. In the present embodiment, since the adjusting device circulates according to the set threshold value which is preset, the cavitation coefficient values and the set steps, and obtains the finally-determined cavitation intensity value, the whole adjusting process is quick, and the difference between the cavitation intensity value determined after the adjustment and the target cavitation intensity value is quite small; and therefore, the adjusting method of the present embodiment has advantages of high adjusting speed, high error adjusting speed and accurate adjusting result.

Embodiments of the present disclosure further provide a specific example of a method for adjusting ultrasonic cavitation intensity, and the example is based on any of the above embodiments. In the specific example, cavitation parameters influencing the cavitation intensity value are set to include Frequency, Pulse Length, PRF, Pulse Times, Line Density, ROI Size and Transmit Voltage, and then the cavitation intensity value can be calculated through the formula (3).

Here, n=4 is further set, and then cavitation coefficients respectively include a first cavitation coefficient, a second cavitation coefficient, a third cavitation coefficient and a fourth cavitation coefficient, where adjusting objects of the first cavitation coefficient are coefficient k1 of the Frequency and coefficient k2 of the Pulse Length; adjusting objects of the second cavitation coefficient are coefficient k3 of the PRF and coefficient k4 of the Pulse Times; adjusting objects of the third cavitation coefficient are the coefficient k5 of the Line Density and coefficient k6 of the ROI Size; and an adjusting object of the fourth cavitation coefficient is coefficient k7 of the Transmit Voltage.

A coefficient value of k1 is −a1, and a negative coefficient value of k1 is a1; a coefficient value of k2 is a2, and a negative coefficient value of k2 is −a2; a coefficient value of k3 is a3, and a negative coefficient value of k3 is −a3; a coefficient value of k4 is a4, and a negative coefficient value of k4 is −a4; a coefficient value of k5 is a5, and a negative coefficient value of k5 is −a5; a coefficient value of k6 is −a6, and a negative coefficient value of k6 is a6; and a coefficient value of k7 is a7, and a negative coefficient value of k7 is −a7; and $0 \leq |a1|, |a2|, |a3|, |a4|, |a5|, |a6|, |a7| \leq 1$. The set threshold value is 0.001. It should be noted that the set threshold value and a1 to a2 can be automatically set by the operator, or can be set by default when the ultrasonic equipment leaves a factory, or can be set by counting historical data according to application conditions of the ultrasonic equipment; and those skilled in the art can understand that setting manners for the set threshold value and a1 to a2 values include but are not limited to the above conditions.

According to the above specific value settings, the adjusting device here acquires a current cavitation intensity value A0, and a needed cavitation intensity value A' input by the operator, then the adjusting device automatically adjusts the cavitation intensity value to A' from A0, and a specific process is as follows.

In Step 1, if the adjusting device calculates that A'>A0, the adjusting device sets k1=−a1, and k2=a2; if the adjusting device calculates that A'≤A0, the adjusting device sets k1=a1, and k2=−a2, so as to achieve the purpose of adjusting the Frequency and the Pulse Length; and the first cavitation intensity value A1 is obtained through calculation; if |A1−A'|<0.001, the adjustment is stopped, otherwise Step 2 is continued.

In Step 2, if the adjusting device calculates that A'>A1, the adjusting device sets k3=a3, and k4=a4; if the adjusting device calculates that A'≤A1, the adjusting device sets k3=−a3, and k4=−a4, so as to achieve the purpose of adjusting the PRF and the Pulse Times; and the second cavitation intensity value A2 is obtained through calculation; if |A2−A'|<0.001, the adjustment is stopped, otherwise Step 3 is continued.

In Step 3, if the adjusting device calculates that A'>A2, the adjusting device sets k5=a5, and k6=−a6; if the adjusting device calculates that A'≤A2, the adjusting device sets k5=−a5, and k6=a6, so as to achieve the purpose of adjusting the Line Density and the ROI Size; and the third cavitation intensity value A3 is obtained through calculation; if |A3−A'|<0.001, the adjustment is stopped, otherwise Step 4 is continued.

In Step 4, if the adjusting device calculates that A'>A3, the adjusting device sets k7=a7; if the adjusting device calculates that A'≤A3, the adjusting device sets k7=−a7, so as to achieve the purpose of adjusting the Transmit Voltage; and the fourth cavitation intensity value A4 is obtained through calculation; if |A4−A'|<0.001, the adjustment is stopped, otherwise Step 5 is continued.

In Step 5, ½ of a step length is taken and step 1 to step 4 are repeated until |Ai−A'|<0.001; in this repeated circulation, k1 in a second adjustment is one half of a1 in a first adjustment, and k2 is one half of a2 in the first adjustment, . . . , and so on; k1 in a third adjustment is one half of a1 in a previous adjustment, k2 is one half of a2 in a previous adjustment.

The above specific examples are embodiments of the present disclosure; those skilled in the art can understand that they can further obtain the target cavitation intensity value in a manner of modifying cavitation parameters or modifying cavitation coefficients or adjusting cavitation coefficients, namely, resetting related values or adjusting sequences, according to technical solutions provided by embodiments of the present disclosure, which are not described redundantly here.

Embodiment 3

Figure 3:
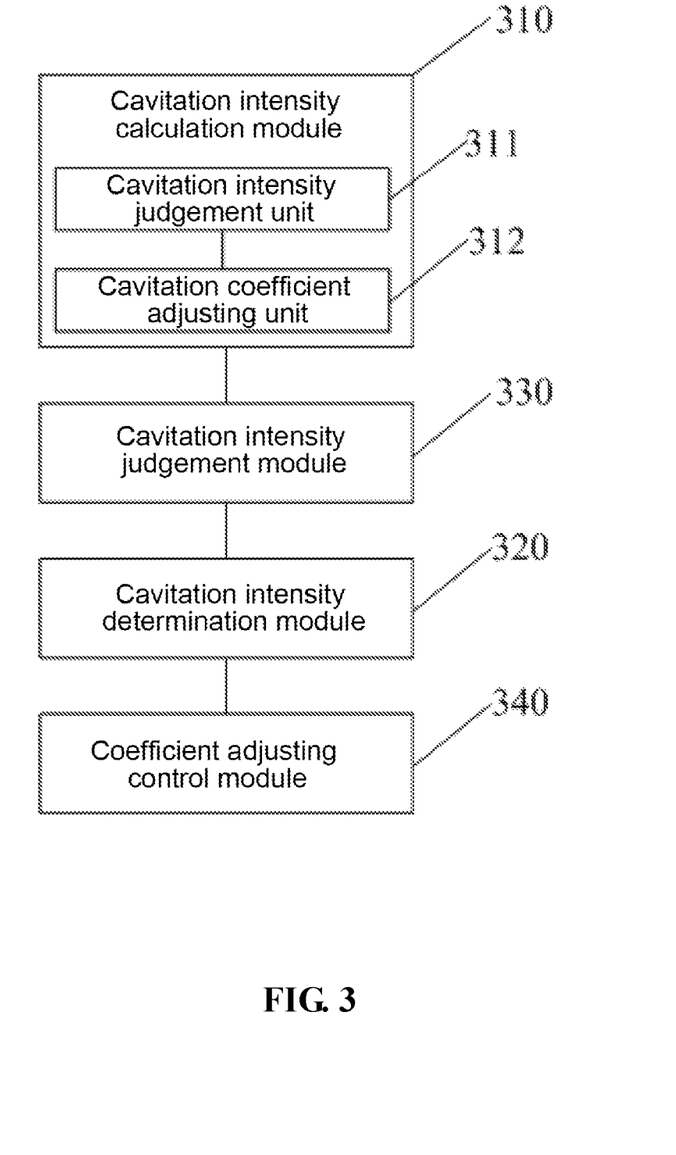
FIG. 3 is a schematic diagram illustrating a device for adjusting ultrasonic cavitation intensity provided by embodiment 3 of the present disclosure.

FIG. 3 is a schematic diagram illustrating a device for adjusting ultrasonic cavitation intensity provided by embodiment 3 of the present disclosure. Technical solutions of the present embodiment is applicable to a case of automatically adjusting cavitation parameters according to a known target cavitation intensity value; and the device can be configured to execute the method for adjusting ultrasonic cavitation intensity in any of the above embodiments, and the device can be configured in an ultrasonic equipment.

A device for adjusting ultrasonic cavitation intensity provided by the present embodiment includes: a cavitation intensity calculation module 310 and a cavitation intensity determination module 320.

The cavitation intensity calculation module 310 is configured to control to adjust a $j^{th}$ cavitation coefficient according to an $i^{th}$ cavitation intensity value and a target cavitation intensity value, so as to calculate to obtain an $(i+1)^{th}$ cavitation intensity value, where i=0, 1, 2 . . . , j=1, 2, . . . n, and 7≥n≥2; and the cavitation intensity determination module 320 is configured to return the method and continue to calculate to obtain a cavitation intensity value if the absolute value of the difference between the $(i+1)^{th}$ cavitation intensity value and the target cavitation intensity value is greater than a set threshold value, until it is determined that the absolute value of the difference between the obtained cavitation intensity value and the target cavitation intensity value is less than or equal to the set threshold value.

Optionally, the $j^{th}$ cavitation coefficient includes any one or more of transmit frequency coefficient k1, pulse length coefficient k2, pulse frequency coefficient k3, pulse times coefficient k4, scanning line density coefficient k5, region-of-interest size coefficient k6, and transmit voltage coefficient k7.

Optionally, the calculation formula of the cavitation intensity calculation module for calculating the cavitation intensity value Q is specifically as follows:

$$Q = f \begin{pmatrix} ((1+k1) \times \text{Frequency})^{-1/2} \times (1+k2) \times \text{Pulse Length}, \\ (1+k3) \times PRF \times (1+k4) \times \text{Pulse Times}, \\ (1+k5) \times \text{Line Density} \times ((1+k6) \times ROI \text{ Size})^{-1}, \\ \frac{1}{2} \times P((1+k7) \times \text{Transmit Voltage})^2 / Z \end{pmatrix}$$

where the Frequency represents ultrasonic transmit frequency, the Pulse Length represents ultrasonic transmit pulse length, the PRF represents ultrasonic transmit pulse repetition frequency, the Pulse Times represents ultrasonic transmit pulse continuous times, the Line Density represents ultrasonic transmit scanning line density, the ROI Size represents ultrasonic cavitation busting region-of-interest size, and the Transmit Voltage represents ultrasonic transmit voltage.

Optionally, the cavitation intensity calculation module 310 includes: a cavitation intensity judgement unit 311 and a cavitation coefficient adjusting unit 312.

The cavitation intensity judgement unit 311 is configured to judge whether the target cavitation intensity value is greater than the $i^{th}$ cavitation intensity value; and the cavitation coefficient adjusting unit 312 is configured to control to correspondingly adjust a value of the $j^{th}$ cavitation coefficient as a $j^{th}$ coefficient value set according to a set rule when the target cavitation intensity value is greater than the $i^{th}$ cavitation intensity value, so as to calculate to obtain the $(i+1)^{th}$ cavitation intensity value, and control to correspondingly adjust a value of the $j^{th}$ cavitation coefficient as a negative $j^{th}$ coefficient value set according to a set rule when the target cavitation intensity value is less than or equal to the $i^{th}$ cavitation intensity value, so as to calculate to obtain the $(i+1)^{th}$ cavitation intensity value.

Optionally, the set rule includes the following. A $j^{th}$ coefficient value in a next adjustment is 1/m of a $j^{th}$ coefficient value in a previous adjustment, where m>1.

Optionally, an absolute value of the $j^{th}$ coefficient value is greater than or equal to 0, and less than or equal to 1.

Optionally, the adjusting device further includes: a cavitation intensity judgement module 330.

The cavitation intensity judgement module 330 is configured to calculate a difference between the $(i+1)^{th}$ cavitation intensity value and the target cavitation intensity value after the $(i+1)^{th}$ cavitation intensity value is obtained through calculation, and judge whether an absolute value of the difference is less than or equal to the set threshold value.

Optionally, the adjusting device further includes: a coefficient adjusting control module 340.

The coefficient adjusting control module 340 is configured to control to stop adjustment for cavitation coefficients if the absolute value of the difference between the $(i+1)^{th}$ cavitation intensity value and the target cavitation intensity value is less than or equal to the set threshold value.

Optionally, the set threshold value is 0.001.

In the present embodiment, the adjusting device obtains the target cavitation intensity value, and achieves the purpose of adjusting an initial cavitation intensity value to the target cavitation intensity value by adjusting cavitation coefficients; and cavitation coefficients are adjusted according to the target cavitation intensity value in a manner of reverse mapping, and the adjusting manner has advantages of high adjusting speed and quite small adjusting error.

Embodiments of the present disclosure further provide an ultrasonic equipment; the device for adjusting the ultrasonic cavitation intensity in any of the above embodiments is configured in the ultrasonic equipment; and the ultrasonic equipment further includes a display panel. The device for adjusting the ultrasonic cavitation intensity can execute the method for adjusting the ultrasonic cavitation intensity in any of the above embodiments. The ultrasonic equipment can be applied to fields of medical ultrasonic equipment imaging and therapy as a medical instrument, and can also be applied to laboratories and other places as a cleaning equipment.

It should be noted that the adjusting device acquires the initial cavitation intensity value and the target cavitation intensity value input by the operator from the display panel, adjusts the cavitation intensity value of the ultrasonic equipment according to the method for adjusting the ultrasonic cavitation intensity, and adjusts to enable the absolute value of the difference between the finally-determined cavitation intensity value and the target cavitation intensity value to be less than or equal to the set threshold value; and at this moment, the adjusting device controls to complete the adjustment, and the current cavitation intensity value of the ultrasonic equipment is the finally-determined cavitation intensity value. After the adjustment is completed, the adjusting device may transmit a completion instruction to the display panel of the ultrasonic equipment, then the display panel displays adjusting completion information according to the completion instruction, the operator views the adjusting completion information so as to determine that the adjustment is completed, and then the operator operates the ultrasonic equipment to execute a working process.

It should be noted that the above descriptions are merely optional embodiments and the applied technical principles of the present disclosure. Those skilled in the art may understand that the present disclosure is not limited to the specific embodiments here, and for those skilled in the art, various apparent modifications, readjustments and substitutions could be made without departing from the protection scope of the present disclosure. Therefore, although the present disclosure is illustrated in detail through the above embodiments, the present disclosure is not merely limited to the above embodiments; and more other equivalent embodiments can be further included without departing from the concept of the present disclosure, and the scope of the present disclosure is decided by the scope of the attached claims.

What is claimed is:

1. A method for adjusting ultrasonic cavitation intensity, the method being performed by ultrasonic equipment, the ultrasonic equipment comprising at least one processor and a computer-readable storage medium storing instructions executable by the at least one processor, the instructions when executed by the at least one processor causes the ultrasonic equipment to perform the method which comprises:

collecting an initial cavitation intensity value and a target cavitation intensity value;

performing an iterative process of adjusting a $j^{th}$ combination of at least one selected from a group consisting of n cavitation coefficients according to an $i^{th}$ cavitation intensity value and a target cavitation intensity value, and calculating to obtain an $(i+1)^{th}$ cavitation intensity value, wherein i=0, 1, 2 . . . , j=1, 2, . . . , n, and 7≥n≥2, wherein when i=0, the $i^{th}$ cavitation intensity value is the initial cavitation intensity value; and determining whether an absolute value of a difference between the $(i+1)^{th}$ cavitation intensity value and the target cavitation intensity value is greater than a set threshold value, and ending the iterative process in response to determining that the absolute value of the difference between the $(i+1)^{th}$ cavitation intensity value and the target cavitation intensity value is less than or equal to the set threshold value.

2. The adjusting method according to claim 1, wherein, the $j^{th}$ combination comprises at least one selected from the group consisting of a transmit frequency coefficient k1, a pulse length coefficient k2, a pulse frequency coefficient k3, a pulse times coefficient k4, a scanning line density coefficient k5, a region-of-interest size coefficient k6, and a transmit voltage coefficient k7.

3. The adjusting method according to claim 1, wherein, adjusting the $j^{th}$ combination of at least one selected from the group consisting of the n cavitation coefficients according to the $i^{th}$ cavitation intensity value and the target cavitation intensity value, so as to calculate to obtain the $(i+1)^{th}$ cavitation intensity value, comprises:

judging whether the target cavitation intensity value is greater than the $i^{th}$ cavitation intensity value;

controlling to correspondingly adjust a value of each in the $j^{th}$ combination as a corresponding coefficient value set according to a set rule if the target cavitation intensity value is greater than the $i^{th}$ cavitation intensity value, so as to calculate to obtain the $(i+1)^{th}$ cavitation intensity value; and, controlling to correspondingly adjust the value of each in the $j^{th}$ combination to a corresponding negative coefficient value set according to a set rule if the target cavitation intensity value is not greater than the $i^{th}$ cavitation intensity value, so as to calculate to obtain the $(i+1)^{th}$ cavitation intensity value.

4. The adjusting method according to claim 3, wherein, the set rule comprises: a coefficient value in a next adjustment is 1/m of a coefficient value in a previous adjustment, wherein m>1.

5. The adjusting method according to claim 3, wherein, an absolute value of each in the $j^{th}$ combination is greater than or equal to 0, and less than or equal to 1.

6. The adjusting method according to claim 1, wherein, after calculating to obtain the $(i+1)^{th}$ cavitation intensity value, further comprising:

calculating a difference between the $(i+1)^{th}$ cavitation intensity value and the target cavitation intensity value and judging whether an absolute value of the difference is less than or equal to the set threshold value.

7. The adjusting method according to claim 1, further comprising: controlling to stop an adjustment for the cavitation coefficients if the absolute value of the difference between the $(i+1)^{th}$ cavitation intensity value and the target cavitation intensity value is less than or equal to the set threshold value.

8. The adjusting method according to claim 1, wherein, the set threshold value is 0.001.

9. The adjusting method according to claim 1, wherein, adjusting the $j^{th}$ combination of at least one selected from the group consisting of the n cavitation coefficients according to the $i^{th}$ cavitation intensity value and the target cavitation intensity value, so as to calculate to obtain the $(i+1)^{th}$ cavitation intensity value, comprises:

judging whether the target cavitation intensity value is greater than the $i^{th}$ cavitation intensity value;

controlling to correspondingly adjust a value of each in the $j^{th}$ combination as a corresponding coefficient value set according to a set rule if the target cavitation intensity value is greater than the $i^{th}$ cavitation intensity value, so as to calculate to obtain the $(i+1)^{th}$ cavitation intensity value; and, controlling to correspondingly adjust the value of each in the $j^{th}$ combination to a corresponding negative coefficient value set according to a set rule if the target cavitation intensity value is not greater than the $i^{th}$ cavitation intensity value, so as to calculate to obtain the $(i+1)^{th}$ cavitation intensity value.

10. The adjusting method according to claim 9, wherein, the set rule comprises: a coefficient value in a next adjustment is 1/m of a coefficient value in a previous adjustment, wherein m>1.

11. The adjusting method according to claim 9, wherein, an absolute value of each in the $j^{th}$ combination is greater than or equal to 0, and less than or equal to 1.

12. A device for adjusting ultrasonic cavitation intensity with ultrasonic equipment, comprising:

at least one processor; and a memory communicably connected with the at least one processor for storing instructions executable by the at least one processor, wherein execution of the instructions by the at least one processor causes the at least one processor to:

collect an initial cavitation intensity value and a target cavitation intensity value;

perform an iterative process of adjusting a $j^{th}$ combination of at least one selected from a group consisting of n cavitation coefficients according to an $i^{th}$ cavitation intensity value and a target cavitation intensity value, so as to calculate to obtain an $(i+1)^{th}$ cavitation intensity value, wherein i=0, 1, 2 . . . , j=1, 2, . . . , n, and 7≥n≥2, wherein when i=0, the $i^{th}$ cavitation intensity value is the initial cavitation intensity value; and determine whether an absolute value of a difference between the $(i+1)^{th}$ cavitation intensity value and the target cavitation intensity value is greater than a set threshold value, and end the iterative process in response to determining that the absolute value of the difference between the $(i+1)^{th}$ cavitation intensity value and the target cavitation intensity value is less than or equal to the set threshold value.

\* \* \* \* \*